United States Patent [19]

Murakami et al.

[11] Patent Number: 4,855,073

[45] Date of Patent: Aug. 8, 1989

[54] LUBRICANT COMPOSITIONS AND METHODS FOR PREPARATION OF SAME

[76] Inventors: Mitsuhiro Murakami, 515, Nishi Tanaka, Gotemba-shi, Shizuoka-ken; Takahiro Mikami, Chuoh Green Town, 767-7, Hagiwara, Gotemba-shi, Shizuoka-ken; Hiroyuki Nagamatsu, 1289-578, Niihashi, Gotemba-shi, Shizuoka-ken; Mitsuji Tokuno, 213-18, Nagatsuka, Gotemba-shi, Shizuoka-ken, all of Japan

[21] Appl. No.: 199,485

[22] Filed: May 27, 1988

[30] Foreign Application Priority Data

Jun. 12, 1987 [JP] Japan ................................ 62-146434

[51] Int. Cl.$^4$ ............................................. C10M 129/10
[52] U.S. Cl. ..................................... 252/39; 252/42.7; 252/56 R; 252/57; 560/64; 560/75
[58] Field of Search ........................ 252/39, 42.7, 56 R, 252/57; 560/64, 75

[56] References Cited

U.S. PATENT DOCUMENTS

| | | | |
|---|---|---|---|
| 2,194,478 | 3/1940 | Moser et al. | 252/57 |
| 3,014,868 | 12/1961 | Munns et al. | 252/39 |
| 3,954,808 | 5/1976 | Elliott et al. | 252/57 |
| 4,263,167 | 4/1981 | Mazo | 252/57 |

*Primary Examiner*—Jacqueline V. Howard
*Attorney, Agent, or Firm*—Klein & Vibber

[57] ABSTRACT

Disclosed are a lubricant composition comprising a major amount of one or more lubricant fluids and at least one polyvalent metal salt of the formaldehyde condensation products of $C_{12}$–$C_{22}$ alkyl hydroxy benzoic acid, and a method of preparation of same. Because of the methylenebis structure of the polyvalent metal salts, engine properties such as detergency/dispersancy, thermal stability, hydrolytic stability, oil solubility and especially compatibility with other additives are improved by the use of the composition.

19 Claims, No Drawings

LUBRICANT COMPOSITIONS AND METHODS FOR PREPARATION OF SAME

FIELD OF THE INVENTION

The present invention generally relates to new and excellent lubricant compositions having improved engine properties such as detergency/dispersancy, thermal stability, hydrolytic stability, oil solubility, and especially compatibility with other additives. More particularly, the present invention relates to lubricant compositions comprising one or more lubricant fluids and polyvalent metal salt of formaldehyde condensation products of $C_{12}$–$C_{22}$ alkyl hydroxy benzoic acid, and a method of preparation of same.

BACKGROUND OF THE INVENTION

Various properties are required for lubricants to be utilized for internal combustion engines. It has become common knowledge to add one or more chemical additives to a lubricant in order to improve engine properties. Depending upon the required properties, various additives such as detergents/dispersants, antioxidants, antifoam agents, viscosity-index improvers, corrosion inhibitors, rust inhibitors and the like have been utilized. Among them, detergents/dispersants are generally added to various lubricants to be used for internal combustion engines and are particularly important.

In recent years, internal combustion engines have been operated continuously for a longer span of time at higher temperatures due to the improvements in structures and materials of engines. This has created a demand for engine oils which may withstand continuous use for a longer span of time at higher temperatures. Improvements of engine oils in various properties, even though they are small in numerical values, have great significance from a practical view point.

Various properties of engine oils are derived from chemical structures of the additives and functional groups contained therein. Different chemical structures may give different properties or characteristics and the increase in kind and number of functional groups included may give different activities. Also it is true that, in proportion, as functional groups in a molecule of an additive compound increase in kind and number, the activities are greatly extended and the effects increase.

PRIOR ART DEFICIENCIES

Conventional detergents/dispersant typically comprise an oil-soluble metal salt as the surface active agent. It is known that the cleansing and dispersing activities of a detergent/dispersants are derived from the polar groups and oleophilic groups included therein. More particularly the polar groups which adsorb insolubles produced in engines during their operation while the oleophilic groups disperse the insolubles adsorbed thereto into oils. Typical polar groups are hydroxyl, sulfonic acid, carboxylic acid, and phosphoric acid. The classification of detergents/dispersants is usually made on the basis of the kind of polar groups included therein. For instance, so-called metal phenate type additives contain a phenolic hydroxyl group, metal sulphonate type additives contain sulfonic acid groups, metal phosphate type additives contain phosphoric acid groups, and metal salicylate type additives contain a hydroxyl group and a carboxylic acid group which are attached to a benzene nucleus at adjacent positions.

As previously mentioned, lubricants must serve several purposes because engine operation is complicated. Thus combined use of two or more kinds of additives often has been made, since the use of a single additive which includes a functional groups too few in kind and number may be insufficient for the required purposes. In such a case, two or more additives are generally used together to provide coaction or synergism therebetween. However, the additives to be jointly used may not be soluble in lubricants without affecting each other. In general, these additives must be mutually soluble, and even though each additive is soluble in oils, they are not always mixed together. The poor solubility of additives individually or jointly in oils may cause turbidity and/or precipitation problems which result in malfunction of the engines. For example, conventional additives of the calcium salt of alkyl hydroxy benzoic acid and additives of the calcium sulfonate type are insoluble jointly, and thus cannot be used jointly because of precipitation problems.

Moreover, the operating conditions of engines become ever more severe, and require lubricants which can withstand higher temperatures for a longer span of time. Contamination of engine oils by water causes problems since the intermixed water may promote or enhance hydrolysis of additive compounds at high temperatures. Therefore suitable additives for lubricants are required to be stable against hydrolysis at high temperatures.

Conventional additives generally are inadequate to solve the problems described above.

SOLUTION OF THE PROBLEMS

Accordingly, the inventors have focused upon hydroxy benzoic acid which has together a hydroxyl group and a carboxylic acid group in a molecule, and succeeded in the solution of the foregoing problems at issue by condensing $C_{12}$–$C_{22}$ alkyl hydroxy benzoic acid with formaldehyde. More precisely, the inventors have found that lubricant compositions which include one or more lubricants and polyvalent metal salts of the formaldehyde condensation products of $C_{12}$–$C_{22}$ alkyl hydroxy benzoic acid have desirable properties, including thermal stability at high temperatures, hydrolytic stability, oil solubility, compatibility with other additives, and improved detergency/dispersancy.

OBJECTS OF THE INVENTION

Therefore, it is an object of the present invention to provide new lubricant compositions comprising one or more lubricants whose properties are improved by the polyvalent metal salt formaldehyde condensation products of $C_{12}$–$C_{22}$ alkyl hydroxy benzoic acid.

It is another object of the present invention to provide new lubricant compositions which are excellent in detergency/dispersancy at high temperatures, and which have improved thermal stability, hydrolytic stability and oil solubility.

It is a further object of the present invention to provide new lubricant compositions which can be economically prepared without complicated anti-pollution measures.

DETAILED DESCRIPTION OF THE INVENTION

According to the present invention, it is possible to produce lubricant compositions which are excellent in detergency/dispersancy, thermal stability, hydrolytic stability and oil solubility.

As the lubricant compositions of the present invention have many useful properties by themselves, it is possible to reduce the kinds of additives to be jointly used. Also lubricant compositions of the present invention can be utilized for various types of engines on land or at sea since they are multipurpose lubricants.

The active sites on the benzene ring which can be substituted by alkyl groups in the alkylation of phenol are the ortho and/or the para positions with respect to the hydroxyl group. The active sites of an alkyl phenol for substitution by carboxylic acid groups are the ortho para positions with respect to the hydroxyl group. The active sites of an alkyl hydroxy benzoic acid for substitution by the methylene groups of formaldehyde are also the ortho para positions with respect to the hydroxyl group.

Therefore, in order to achieve an efficient condensation reaction of alkyl hydroxy benzoic acid with formaldehyde, it is necessary that the alkyl phenol prepared by alkylation of phenol be a monoalkyl phenol substituted by only a single alkyl group. If the monoalkyl phenol can be efficiently prepared, the condensation reaction of the monoalkyl benzoic acid formed from monoalkyl phenol with formaldehyde will be efficiently carried out. Consequently the methylenebis structure sought by the present invention can be formed by bonding two molecules of alkyl hydroxy benzoic acid with the interposition of a methylene group from formaldehyde.

Thus it will be understood that the polyvalent metal salt of formaldehyde condensation products of alkyl hydroxy benzoic acid prepared in accordance with the present invention contain two hydroxyl groups and two carboxylic acid groups as the polar groups and two alkyl groups as oleophilic groups, all in the same molecule. It will be also understood that if the polyvalent metal salt of alkyl hydroxy benzoic acid originally had excellent detergency/dispersancy, thermal stability and hydroytic stability characteristics, these are further increased by the formation of methylenebis structure by the present invention. Moreover, oil solubility and compatibility with other additives are also improved.

The process of the present invention includes the following steps:

(1) preparation of a monoalkyl phenol by the alkylation of phenol with a $C_{12}$–$C_{22}$ olefin in the presence of an ion exchange resin alkylation catalyst;

(2) preparation of a metal phenoxide by addition of caustic alkali to the resulting reaction mixture containing monoalkyl phenol followed by removal of water produced as a byproduct;

(3) carboxylation by the reaction of carbon dioxide with the metal phenoxide obtained in step (2) under pressure, followed by hydrolysis with addition of mineral acids to make an isolate alkyl hydroxy benzoic acid;

(4) condensation of the collected alkyl hydroxy benzoic acid with formaldehyde in the presence of a reaction promoter, followed by the isolation and the removal of the unreacted formaldehyde and the reaction promoter;

(5) preparation of the alkali salt of the resulted condensation products by the addition of caustic alkali, followed by converting into the corresponding polyvalent metal salt by double decomposition by the addition of polyvalent metal chlorides.

The above steps are summarized by the following reaction scheme:

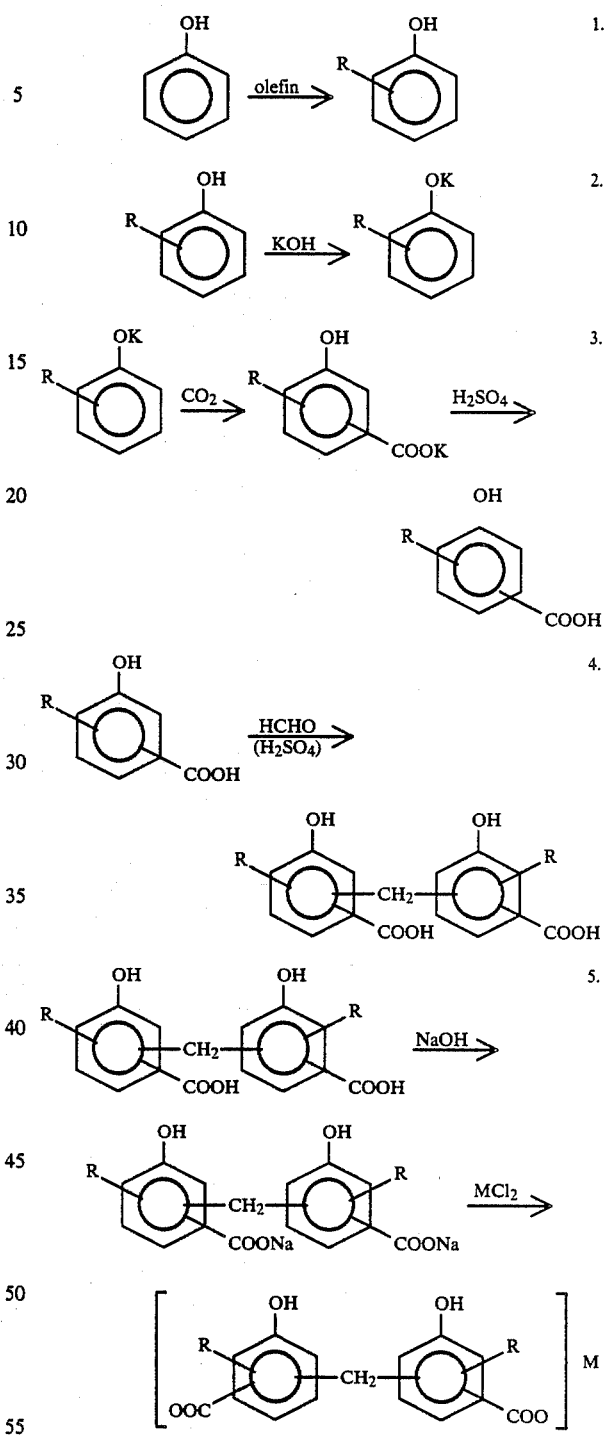

If desired, a further step described below can be added, as follows:

(6) a step of conversion of the resulted polyvalent metal salt into a highly basic salt by the addition of an alcoholic suspension of polyvalent metal hydroxides and blowing of carbon dioxide gas thereto.

Addition of one or more lubricants can be made during steps(5) and/or (6) above. Similarly, the salts can be isolated in known manner if desired.

More specifically, in accordance with the present invention, phenol as the starting substance is subjected to alkylation with an alkylation agent in the presence of catalysts. Olefins with $C_{12}$–$C_{22}$ (preferably $C_{14}$–$C_{18}$) can be utilized as the alkylation agents.

Heretofore, activated clay, metal chlorides, hydrofluoric acid, phosphoric acid and the like have been utilized as alkylation catalysts. Above all, activated clay has been widely used for the reasons of ease of handling and low cost. However, as activated clay remains in reaction system, its use requires filtration and disposal steps and anti-pollution measures. All other liquid inorganic acids are highly dangerous substances, and are dangerous to handle. Recently, ion-exchange resins in the form of solid organic acids useable as catalysts for alkylation became available in the market. In Japanese Patent Application No. 84,102/59 (1984), it is disclosed that highly acidic sulfonated polystyrene-type resins are excellent as alkylation catalysts among the acidic ion-exchange resins. They have a longer life cycle, are reusable and are highly advantageous from the view point of anti-pollution measures. More importantly they can be used to prepare predominantly monoalkyl phenols in high yields. One such catalyst, DIAION RCP-145H (by Mitsubishi Kasei Company) has been sold in the market, and found to be suitable as the alkylation catalyst for the present invention.

For example, this catalyst can be added to a mixture of 2-3 moles of phenol and 1 mole of olefin, and the resulting mixture subjected to alkylation at a temperature between 90°14 150° C., preferably 110°–135° C., for 2-3 hours to yield 95-98 mol. % of monoalkyl phenols. The quantity of the catalyst to be used ranges between 3–10 wt. %, of total quantity of phenol and olefin. Comparative yields of monoalkyl phenol in cases where DIAION RCP-145H, activated clay and the combination of activated clay and phosphoric acid were utilized, are shown in the following table.

| catalyst | DIAION RCP-145H | activated clay | activated clay and phosphoric acid |
|---|---|---|---|
| ratio of olefin to phenol | 0.5 | 0.5 | 0.5 |
| quantity of catalyst (wt. %) | 4 | 6 | 3 |
| reaction temperature (°C.) | 100 | 160 | 120 |
| reaction hours | 2 | 6 | 3 |
| yield of monoalkyl phenols (mole %) | 97 | 75 | 80 |

The thus resulting monoalkyl phenol is converted into alkyl hydroxy benzoic acid via metal phenoxide as the intermediate product by the well-known Kolbe-Schmitt reaction. For example, to 1 mole of alkyl phenol, 1 mole of caustic alkali is added, the resulted mixture is reacted at 60°–65° C. for about 1 hour, then the temperature of the reaction mixtures increased to 200° C. to remove byproduct water. The resulting reaction mixture is placed into an autoclave, and 1.5-2.2 moles of carbon dioxide gas is blown into said mixture under 5-15 atmospheric pressure at 140°–180° C. for 1-3 hours. After the reaction, 30-50% of sulfuric acid is added for hydrolysis and the resulting alkyl hydroxy benzoic acid is isolated and collected.

The resulting alkyl hydroxy benzoic acid is subjected to a condensation reaction with formaldehyde in the presence of concentrated sulfuric acid as the reaction promoter. Commercially available Formalin is easy to handle and can be utilized as the formaldehyde source.

Thus, for example, to 1 mole of alkyl hydroxy benzoic acid 20–50 wt. % of concentrated sulfuric acid and 0.5–4 moles of formaldehyde are added and the resulting mixture is condensed at 20°–100° C. for about 3–5 hours. During the condensation reaction, an aliphatic hydrocarbon, such as hexane and heptane, which does not participate or contribute to the reaction, can be added. After the condensation reaction, unreacted formaldehyde and sulfuric acid are isolated and removed from the mixture, and the remaining mixture is washed with sufficient water. For complete isolation, it is preferable to dilute the reaction mixture with an aromatic hydrocarbon such as benzene and toluene. Thus the condensation products of alkyl hydroxy benzoic acid with formaldehyde are obtained.

Mineral oil is added to the resulting condensation products, to prepare a 100–180 wt. % mineral oil solution of the condensation products. Caustic alkali is added to said resulting solution to convert the resulting condensation products into the corresponding alkali salts. A methanol solution of polyvalent metal chloride is added to the resulting solution, and the resulting mixture is kept at the reflux temperature of methanol for about 1 hour. Then the temperature of the solution is elevated to above 110° C. to remove volatile substances, and thereby obtain a mineral oil solution of the polyvalent metal salt of the formaldehyde condensation products of alkyl hydroxy benzoic acid.

Although magnesium, calcium, strontium or barium and mixtures thereof can be utilized as the polyvalent metals, calcium is preferred.

When a salt prepared in accordance with the present invention is utilized as an additive for lubricants, it is preferable to use it in the form of basic salts or of highly basic salts. Basic or highly basic salts can be prepared by adding a methanol suspension of polyvalent metal hydroxide to the polyvalent metal salt of the formaldehyde condensation products of alkyl hydroxy-benzoic acid, and $CO_2$ is reacted at 20°–30° C. with the resulting mixture. The quantities of polyvalent metal hydroxide and carbon dioxide to be used are determined by the desired base number.

The term "basic" is determined by the excess amount of polyvalent metal in a unit weight of the polyvalent metal salt of the condensation product compared to that in the corresponding neutral salt. Total base number (TBN) is represented by the number in milligrams of KOH corresponding to the equivalent quantity of acid which is required to neutralize the total alkaline content in 1 g of the salt. In general, the present lubricant additives are used in their highly basic forms for the additional purpose of neutralizing acids produced in engines. The degree of highly basic state is also represented by the term "metal ratio" which is determined by the following formula:

metal ratio=(equivalent of metal/equivalent of organic acid) −1.

Therefore, the metal ratio of a neutral salt is zero. The range of metal ratios of the lubricant compositions in accordance with the present invention is between 0–8, and preferably is 3–5.

The lubricants to be included in the lubricant composition of the present invention can be mineral oils, synthetic lubricants, fatty oils derived from animals and plants, but petroleum lubricants as mineral oils are preferred. The kind and quantity of lubricants to be added may vary depending upon the various purposes, for instance, for the purpose of adjusting the viscosity during the process and of regulating the TBN during the final process of the preparation of the composition in accordance with the present invention as the product for sale.

The precise amounts of the polyvalent metal salts of the invention to be used in the instant lubricating compositions can vary depending on the quantity of lubricant added in steps 5 or 6 of the above-disclosed method. A workable and more effective range can be from about 0.1 to 10% or more based on the total composition. The lubricant additives of the present invention can be utilized in conjunction with other additives such as detergents/dispersants, anti-oxidants, viscosity-index improvers, foam inhibitors and so on.

The invention is further disclosed in non-limiting fashion by the following examples.

EXAMPLES 1-6

Monoalkyl phenol was prepared in such a manner that to respective mixtures consisting of the quantities of olefin and the quantity of phenol shown in table 1, a quantity of DIAION RCP-145H was added as a catalyst. The resulting mixtures were subjected to an alkylation reaction under agitation at a suitable velocity necessary to eliminate sedimentation of the catalyst at 110° C. for 2 hours, then the reacted mixtures were subjected to vacuum distillation at 5 mm Hg. The quantities of reaction components and yields of monoalkyl, phenol are shown in Table 1.

dehyde were added under agitation. The resulting mixtures were reacted under a nitrogen gas atmosphere at 65° C. for 5 hours. After removing hexane from each mixture, the residues were diluted with same quantity of xylene. After settling the resulting mixtures, sulfuric acid and unreacted formaldehyde were removed by decantation. From each residue, xylene was removed by distillation to thereby obtain each condensation product. To the resulting condensation products, mineral oil was added to adjust the condensation products to TAN 65. The resulting solutions each were neutralized with sodium hydroxide to form mineral oil solutions of the corresponding sodium salt. Then respective calcium chloride dissolved in fourfold quantities of methanol were added thereto. After keeping the resulting mixtures at the reflux temperature of methanol for 1 hour to cause double decomposition, the temperature of the resulting reaction mixture was elevated while blowing nitrogen gas to remove methanol. After cooling the resulting mixtures to room temperature, they were diluted with the same quantity of xylene, then subjected to filtration to remove the sodium chloride produced. To the resulting xylene solutions containing the calcium salt of the condensation products of alkyl hydroxy benzoic acid with formaldehyde, the indicated quantities of slaked lime and fivefold quantities, with respect to the amounts of slaked lime, of methanol were added, and the indicated quantities of carbon dioxide gas were blown thereinto at 20°-30° C. Methanol was distilled

TABLE 1

| Example | phenol (g) | olefin (g) | catalyst (g) | monoalkyl phenol yield (mole %) | carbon atoms included in olefin |
|---|---|---|---|---|---|
| 1 | 280 | 210 | 23.5 | 90 | 10* |
| 2 | " | 252 | 25.5 | 97 | 12 |
| 3 | " | 294 | 27.5 | 97 | 14 |
| 4 | " | 336 | 29.5 | 98 | 16 |
| 5 | " | 346 | 30.0 | 95 | 15-20 |
| 6 | " | 357 | 30.5 | 96 | 16-18 |

*The olefin used in example 1 is out of the range of the present invention.

EXAMPLES 7-12

Using the respective monoalkyl phenols prepared in examples 1-6, the following process was carried out under the same conditions. To a quantity of the respective monoalkyl phenol, the amount of caustic alkali shown in table 2 was added with heating to 50° C. The resulting mixtures were reacted at 65° C. for 1 hour, then nitrogen gas was blown into the reacted mixtures with gradual elevation of the temperature up to 200° C. and maintained at this temperature for 2 hours to remove water produced as a byproduct. After cooling the resulting reaction mixtures were poured into autoclaves equipped with stirrers. Carbon dioxide gas was blown into the mixtures at 140° C. under 10 atmospheric pressure for 2 hours. After cooling the reaction mixtures to room temperature, they were poured into separatory funnels, and 30% sulfuric acid was gradually added thereto with shaking and stirring, respectively, for neutralization. In this manner alkyl hydroxy benzoic acid was respectively separated and collected from the mixtures.

To the respectively collected alkyl hydroxy benzoic acids, the same quantity of hexane and 50 wt. % of concentrated sulfuric acid were respectively added. To the resulting mixtures, respective quantities of formalout of the resulting mixtures. Then unreacted slaked lime was removed by filtration, and finally xylene was distilled out of the filtrate. The TBN of the final products are shown in Table 2 together with the respective quantities of the materials used in examples 7-12. Samples A-F were assigned to the respective products as shown in table 2 for future reference.

EXAMPLES 13-15

Using monoalkyl phenol prepared in examples 2, 4 and 5, mineral oil solutions of alkyl hydroxy benzoic acid were prepared in the same manner as examples 7-12. The resulting solutions of said acid were individually reacted directly with sodium hydroxide to form the corresponding sodium salt without a condensation process. The mineral oil solutions of the resulting sodium salt were converted into their corresponding calcium salts with calcium chloride. To each resulting calcium salt, slaked lime and methanol were added, then carbon dioxide gas was blown thereinto to obtain mineral oil solutions of highly basic calcium salt. The TBN's of the final products are also shown in Table 2, together with the respective quantities of the materials used in examples 13-15. Furthermore, samples G-I were assigned to the respective final products as shown in Table 2 for reference in the descriptions below:

TABLE 2

| example | alkyl phenol (g) | KOH (g) | $CO_2$ (g) | formalin (g) | $CaCl_3$ (g) | slaked lime (g) | $CO_2$ (g) | final products TBN | smpl. name |
|---|---|---|---|---|---|---|---|---|---|
| 7 | 200 | 56.1 | 75.2 | 256 | 59.5 | 85.5 | 60.7 | 175 | A* |
| 8 | " | 50.0 | 67.2 | 229 | 53.1 | 76.3 | 54.2 | 170 | B |
| 9 | " | 45.3 | 60.7 | 207 | 40.8 | 69.0 | 49.0 | 175 | C |
| 10 | " | 41.3 | 55.4 | 187 | 43.8 | 62.9 | 44.7 | 180 | D |
| 11 | " | 40.4 | 54.2 | 185 | 42.8 | 61.5 | 43.7 | 172 | E |
| 12 | " | 39.5 | 53.0 | 181 | 41.9 | 60.2 | 42.8 | 177 | F |
| 13 | " | 50.0 | 67.2 | — | 53.1 | 76.3 | 54.2 | 173 | G* |
| 14 | " | 41.3 | 55.4 | — | 43.8 | 62.9 | 44.7 | 174 | H* |
| 15 | " | 40.4 | 54.2 | — | 42.8 | 61.5 | 43.7 | 178 | I* |

*The samples A, G, H and I are not included in the scope of the present invention.

With respect to the samples A–I, engine property tests were conducted as follows:

(1) ENGINE TEST

To 9 lots of a parafinic mineral oil, respective samples were added to prepare 9 kinds of test oils of SAE 30, TBN 7. To each test oil, 0.6 wt. % of antioxidant (zinc dialkyl dithiophosphate) was added. Using a diesel engine (by YANMAR, NSA-40C), the engine properties of the test oils were tested.

| SPECIFICATION OF THE ENGINE | |
|---|---|
| type: | 4 cycle, horizontal, water-cooled |
| maximum power: | 5 PS |
| engine speed: | 2400 r.p.m. |
| bore: | 70 mm |
| stroke: | 70 mm |
| TEST CONDITIONS | |
| power: | 3.5 PS |
| engine speed: | 2200 r.p.m. |
| temperature of crank case water: | 90° C. |
| test period: | 100 hours |
| fuel: | gas oil (containing 0.5 wt. % sulfur) |
| fuel consumption: | 650–750 ml/h |

EVALUATION OF THE ADDITIVES OF THE INVENTION

The quantities and qualities of sludge and lacquer stuck on the pistons were observed, and the appearance was evaluated by the demerit mark method, which rates the best performance by 10.

The percentages of the composition of samples A–I added to the respective lubricants are 4.0 wt. %.

The results are shown in Table 3.

TABLE 3

| sample | A | B | C | D | E | F | G | H | I |
|---|---|---|---|---|---|---|---|---|---|
| evaluation | 8.7 | 9.0 | 9.3 | 9.2 | 9.2 | 9.2 | 8.6 | 8.5 | 8.8 |

As shown in Table 3, the best performances were those of the samples of this invention (B,C,D,E,F).

(2) PANEL COKER TEST

To 9 lots of a parafinic mineral oil, various samples of salts were added to prepare 9 kinds of test oils having values of SAE 30 and TBN 7. The panels used were made of duralumin.

| TEST CONDITIONS | |
|---|---|
| temperature of panel: | 300° C. |
| temperature of oil: | 110° C. |
| test period: | 3 hours |
| splash condition: | splashing 15 sec./ pausing 60 sec. |

The results are shown in Table 4.

TABLE 4

| samples | A | B | C | D | E | F | G | H | I |
|---|---|---|---|---|---|---|---|---|---|
| accumulation | 6.3 | 5.0 | 8.0 | 9.7 | 9.9 | 2.0 | 24.5 | 40.0 | 31.1 | unit: mg (3) OXIDATION STABILITY TEST

To 9 lots of a parafinic mineral oil, samples of salts were added to prepare 9 kinds of test oils having values of SAE 30 and TBN 7. The tests were carried out in accordance with JIS 2514, at 165.5° C. for 48 hours. Viscosity increasing ratio at 40° C. and increasing tendency of total acidity (mg KOH/g) were observed.

The results are shown in Table 5.

TABLE 5

| samples | A | B | C | D | E | F | G | H | I |
|---|---|---|---|---|---|---|---|---|---|
| viscosity ratio | 1.20 | 1.18 | 1.14 | 1.14 | 1.15 | 1.12 | 1.27 | 1.30 | 1.25 |
| increase of acidity | −0.35 | −0.30 | −0.80 | −0.45 | −0.50 | −0.90 | 0.30 | 0.36 | 0.25 |

(4) HYDROLYTIC STABILITY TEST

To 9 lots of a parafinic mineral oil, samples of salts were added to prepare 9 kinds of test oils of SAE 30 and TBN 7. To each test oil, 0.6 wt. % of an antioxidant (zinc dialkyl dithiophosphate) was added. The test was carried out in accordance with the modified ASTM D 3619 procedure so that 100 g of respective test oils were poured into each bottle together with 5 g of water, and sealed. The sealed bottles were rotated upside down at a velocity of 5 r.p.m. at 93° C. for 24 hours to make the contents deteriorate. The deteriorated test oils were centrifuged at 12,000 r.p.m. for 1 hour. The retaining TBN ratio of each of the respective supernatants were measured.

The results are shown in Table 6.

TABLE 6

| samples | A | B | C | D | E | F | G | H | I |
|---|---|---|---|---|---|---|---|---|---|
| TBN retention (%) | 88 | 90 | 95 | 95 | 93 | 90 | 83 | 88 | 86 |

(5) COMPATIBILITY TEST WITH SULFONATE ADDITIVE

To 9 lots of a parafinic mineral oil, samples of the salts and a sulfonate type additive were added in the ratio of 1:1 to prepare 9 kinds of test oils of SAE 30 and TBN 20 (0.6 wt. % of antioxidant was added to each). The viscosity index of the mineral oil was 106 (for severe tests). The test oils were kept 60 days under cyclic test conditions, initially at 60° C. for 8 hours followed by 5° C. for 16 hours. Successive deterioration was observed with the naked eye. The results are shown in Table 7. Evaluation was made by following the three-stages evaluation criteria below:

THREE-STAGES EVALUATION CRITERIA PROTOCOL
(a) —: substantially transparent,
(b) ±: foggy
(c) +: apparently observed turbidity

TABLE 7

| samples | A | B | C | D | E | F | G | H | I |
|---|---|---|---|---|---|---|---|---|---|
| after 60 days | ± | — | — | — | — | — | + | + | + |

It should be noted that samples A and G–I are comparative samples which are not included within the scope of the present invention.

It will be understood as characterizing the present invention that monoalkyl phenol can be used as the starting substance, that the use of monoalkyl phenol enables to carry out the condensation reaction efficiently and that the methylenebis structure enables to increase the kind and number of functional groups contained in a given molecule.

It will be also understood that the lubricant compositions in accordance with the present invention have desirable properties in various aspects as evident from the foregoing tests and that excellent lubricant compositions thus can be prepared efficiently and economically without requiring anti-pollution measures.

While the present invention has been illustrated mainly by its best modes those skilled in the chemical arts will understand that equivalents thereof may be employed without departing from the spirit and scope of the invention as set forth in the appended claims.

What is claimed is:

1. A lubricating oil additive compound having the generic formula (I):

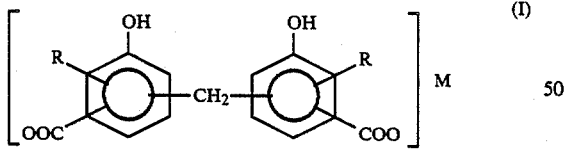

wherein R is a $C_{12}$ to $C_{22}$ alkyl group and M is at least one polyvalent metal selected from the group consisting of magnesium, calcium, strontium and barium; each of said R groups being in the o- or p- position relative to said OH group in the respective benzene ring.

2. The additive according to claim 1, wherein R is a $C_{14}$ to $C_{18}$ alkyl group.

3. The additive according to claim 1, wherein M is calcium.

4. The additive of claim 1, having a metal ratio ranging from 0 to 8.

5. The additive of claim 1, having a metal ratio of 3 to 5.

6. A lubricant additive composition containing from about 50 to 65% by weight of at least one diluent and a minor, effective, amount of at least one polyvalent metal salt of the formaldehyde condensation products of $C_{12}$–$C_{22}$ alkyl hydroxy benzoic acid of the formula (I) of claim 1.

7. A method for preparing a lubricant composition, which contains a major amount of at least one diluent selected from the group consisting of mineral oils, synthetic lubricating oils, fatty oils derived from animals and plants, and a minor amount of a polyvalent metal salt of formaldehyde condensation products of $C_{12}$–$C_{22}$ alkyl hydroxy benzoic acid of formula (I) in claim 1, comprising:

(a) alkylating about 2–3 moles of phenol with 1 mole of an olefin having 12–22 carbon atoms in the presence of about 3–10 wt. % with respect to the amount of phenol and olefin, of an ion exchange resin at about 90°–150° C. for about 2–3 hours to form a monoalkyl phenol; then distilling the resulting reaction mixture to remove unreacted phenol and olefin therefrom;

(b) reacting the resulting reaction mixture containing said monoalkyl phenol with an alkali metal hydroxide at about 60°–65° C. for about one hour to form the corresponding metal phenoxide, and then heating to remove any water of reaction formed;

(c) carboxylating said metal phenoxide with about 1.5 to 2.2 moles of carbon dioxide per mole of phenoxide at about 140°–180° C. under about 5–15 atmospheres of pressure for about 1–3 hours to form the corresponding alkali metal salt of an alkyl hydroxy benzoic acid; adding enough 30–50% sulfuric acid in order to hydrolyze the resulting solution; then collecting and isolating the formed alkyl hydroxy benzoic acid;

(d) condensing said alkyl hydroxy benzoic acid with about 0.5 to 4 moles of formaldehyde in the presence of about 20–50 wt. % of reaction promoter at about 20°–100° C. for about 3–5 hours to form formaldehyde condensation products of $C_{12}$–$C_{22}$ alkyl hydroxy benzoic acid; removing unreacted formaldehyde and said reaction promoter; then, diluting the remaining condensation products with a diluent selected from the group consisting of mineral oils, synthetic lubricating oils and fatty oils derived from animals and plants to form a 100 to 180 wt. % solution of said condensation products; and (e) reacting the solution resulting from step (d) with about 1 mole of caustic alkali; and refluxing the resulting reaction mixture now containing the alkali metal salt of said formaldehyde condensation products with about ½ mole of an alcoholic polyvalent metal chloride solution to form a solution of the corresponding polyvalent metal salt condensation products.

8. The method of claim 7 comprising converting said polyvalent metal salt after step e) into a highly basic salt by adding an alcoholic suspension of a polyvalent metal hydroxide and by blowing carbon dioxide into the resultant solution.

9. The method according to claim 7, comprising adding at least one diluent selected from the group consisting of mineral oils, synthetic lubricating oils and fatty oils derived from animals and plants to the solution obtained at step (e) of claim 7, or at the further step of claim 8.

10. The method according to claim 7, further including the step of adding at least one lubricating oil to the final product to form a lubricating composition.

11. The method according to claim 7, wherein said alkylation is effected at a temperature at 90° to 150° C. for 2-3 hours using an amount of said catalyst ranging from 3-10% of the total phenol and olefin.

12. The method according to claim 7, comprising converting, in step (b) of claim 7, said monoalkyl phenol with heat to the corresponding phenoxide with substantially equimolar amounts of said alkali metal hydroxide.

13. The method according to claim 7, diluting, in step (d) of claim 7, said remaining condensation products with 50-65 wt. %, with respect to the total amount of extracted liquid, of one of said diluents.

14. The method according to claim 7, comprising condensing, in step (d), said isolated alkyl hydroxy benzoic acid with formaldehyde in the presence of concentrated sulfuric acid as the reaction promoter.

15. The method according to claim 7, comprising adding about 0.7-1.5 moles of polyvalent metal hydroxide to the filtrate containing said condensation products of step (e), and reacting the resulting mixture with about 0.9 to 1.3 moles, with respect to said polyvalent metal hydroxide, of carbon dioxide at about 20°-30° C. for about 3-5 hours; then removing unreacted polyvalent metal hydroxide and volatile materials to obtain a highly basic polyvalent metal salt of the formaldehyde condensation products of alkyl hydroxy benzoic acid having formula (I) of claim 1.

16. The method according to claim 7, wherein said alkali metal is selected from the group consisting of sodium and potassium.

17. The method according to claim 7, wherein said polyvalent metal chloride is selected from the group consisting of magnesium, calcium, strontium and barium chlorides.

18. In an improved lubricating oil composition comprising a major proportion of a lubricating oil and a combination of additives in an amount sufficient to achieve each additives' function, the improvement whereby said lubricant oil composition contains an effective amount of the additive composition according to claim 6.

19. The composition of claim 18, wherein said effective amount is at least 0.1 to 10% by weight of said composition.

* * * * *